(12) United States Patent
Weinstein et al.

(10) Patent No.: US 8,815,890 B2
(45) Date of Patent: Aug. 26, 2014

(54) RHINITIS TREATMENT REGIMENS

(76) Inventors: Robert E. Weinstein, Boston, MA (US); Allan M. Weinstein, Potomac, MD (US)

(*) Notice: Subject to any disclaimer, the term of this patent is extended or adjusted under 35 U.S.C. 154(b) by 1588 days.

(21) Appl. No.: 11/848,363

(22) Filed: Aug. 31, 2007

(65) Prior Publication Data

US 2008/0058366 A1 Mar. 6, 2008

Related U.S. Application Data

(60) Provisional application No. 60/824,714, filed on Sep. 6, 2006.

(51) Int. Cl.
*A01N 43/42* (2006.01)
*A61K 31/44* (2006.01)
*A61K 45/06* (2006.01)

(52) U.S. Cl.
CPC .................. *A61K 31/44* (2013.01); *A61K 45/06* (2013.01)
USPC ....................................................... 514/291

(58) Field of Classification Search
USPC ........................................................ 514/291
See application file for complete search history.

(56) References Cited

U.S. PATENT DOCUMENTS

| | | | |
|---|---|---|---|
| 5,116,847 A | 5/1992 | Gilbert et al. | |
| 5,661,142 A | 8/1997 | Naeger | |
| 6,086,914 A | 7/2000 | Weinstein et al. | |
| 2005/0222102 A1* | 10/2005 | Maus et al. | 514/171 |
| 2008/0015241 A1* | 1/2008 | White | 514/400 |

* cited by examiner

*Primary Examiner* — Samira Jean-Louis
(74) *Attorney, Agent, or Firm* — Robert R. Deleault, Esq.; Mesmer & Deleault, PLLC

(57) ABSTRACT

A treatment regimen for rhinitis with rhinorrhea includes a daytime dosage unit containing medication for treating rhinitis and an anticholinergic agent for treating rhinorrhea, and a nighttime dosage unit containing medication for treating rhinitis and an attenuated dosage of anticholinergic agent or no anticholinergic agent. A pharmaceutical package for treating rhinitis with rhinorrhea includes a daytime dosage unit containing a medication for treating rhinitis and an anticholinergic agent for treating rhinorrhea, a nighttime dosage unit containing medication for treating rhinitis and an attenuated dosage of anticholinergic agent or no anticholinergic agent, indicia to distinguish between the daytime dosage unit and the nighttime dosage unit, instructions for coordinating the daytime dosage unit and the nighttime dosage unit as a treatment regimen for treating rhinitis with rhinorrhea, and a unifying container for housing the daytime dosage unit, the nighttime dosage unit, the indicia, and the instructions.

2 Claims, No Drawings

RHINITIS TREATMENT REGIMENS

This application claims the benefit of U.S. Provisional Patent Application No. 60/824,714, filed Sep. 6, 2006.

BACKGROUND OF THE INVENTION

1. Field of the Invention

The present invention relates generally to rhinitis treatment regimens. Particularly, the present invention relates to treatment regimens for rhinitis with rhinorrhea.

2. Description of the Prior Art

Rhinitis refers to an inflammatory disorder of the nasal passages. The symptoms of rhinitis typically consist of sneezing, nasal congestion, rhinorrhea and increased nasal secretions. Rhinitis may be allergic in nature, for example, hay fever occurring seasonally and due to airborne inhalants such as pollens, or non-allergic as in individuals who "appear to be allergic" but prove not to have allergic sensitivities. Individuals with non-allergic or "vasomotor" rhinitis often have persistent and even severe daily symptoms. Rhinitis may also be due to infections, for example as with common colds. Rhinorrhea (runny nose) and excessive secretions that occur with rhinitis are some of the most troublesome symptoms for patients. The act of constantly blowing the nose or wiping away secretions, or coughing consequent to post-nasal drip (secretions running down the back of the nose and into the throat) may, especially for adults, interfere with work or social interaction. Rhinorrhea and postnasal drip are considered challenging and often intractable symptoms for practitioners to effectively treat.

Two types of oral medication are commonly used to treat rhinitis: decongestants and antihistamines. Decongestants commonly used to treat rhinitis include the adrenaline-like agents such as pseudoephedrine. These agents act to constrict vessels in the nasal mucus membranes and thereby decrease tissue swelling and nasal congestion. Although their vasoconstrictor effects result in "opening" of the airways, decongestants do not have a drying effect so as to dry secretions.

Histamine is a mediator released from cells that line the walls of the nasal mucous membranes (mast cells). When released, histamine is known to bind to local receptors and thereby cause sneezing, nasal itching, swelling of the nasal membranes, and increased nasal secretions. Antihistamines block the binding of histamine to histamine-receptors in the nasal membranes. Antihistamines are effective only if given prior to histamine release (once histamine is released and binds to the receptor, it is too late). Although individuals typically take antihistamines after symptoms occur, it is more desirable to dose antihistamine so as to effect therapeutic activity in anticipation of the peak times of histamine release. Individuals with allergic rhinitis commonly experience peak symptoms in the morning hours on awakening, a time concomitant with peak histamine release and coinciding with peak exposure to airborne allergens that stimulate histamine release in sensitive individuals.

The first pharmaceutical entities recognized to have antihistaminic action, now referred to as first-generation antihistamines, have lipophilic chemical properties, which contribute to both a sedating and an anticholinergic, drying effect. Examples of sedating antihistamines are brompheniramine, chlorpheniramine, diphenhydramine, promethazine, and hydroxyzine. The sedating side effects of these antihistamines stimulated the development and marketing of non-sedating, or second-generation, antihistamines. While the newly developed antihistamines are less lipophilic than first-generation antihistamines (conferring a reduction in their ability to cross the blood-brain barrier and thereby cause sedation), second-generation antihistamines have a concomitant diminution of anticholinergic effects and decreased potency for drying secretions and controlling rhinorrhea. Examples of second-generation antihistamines are: loratidine (marketed as Claritin®), fexofenadine (marketed as Allegra®), and cetirizine (marketed as Zyrtec®).

U.S. Pat. No. 6,086,914 of Weinstein et al. teaches formulations for allergic rhinitis which combine such newer non-sedating antihistamines together with a third type of agent, an anticholinergic agent, to result in a dosage unit that is non-sedating and also has a drying effect upon the nasal membranes.

Anticholinergic agents, the third and less commonly used oral entity to treat rhinitis, are exemplified by the belladonna alkaloids atropine and scopolamine, which inhibit the muscarinic action of acetylcholine on structures innervated by postganglionic cholinergic nerves. These agents inhibit the nasal secretory mechanism and cause drying of the nasal membranes. Anticholinergic agents also are known to exert central effects that include papillary dilatation and stimulation and depression of the CNS. Drowsiness is known to occur with high doses of anticholinergic agents, and with therapeutic doses of oral scopolamine, but drowsiness is considered rare with therapeutic doses of other oral anticholinergic agents (USPDI Drug Information for the Health Care Professional, 16th Edition, United States Pharmacopoeia Convention, Inc., 219-235, 1996 Rand McNally, Taunton, Mass.). Anticholinergic pharmaceuticals have been developed which have a limited capacity to pass across lipid membranes, such as the blood-brain barrier, and therefore have a limited capacity to produce central effects, examples being the quaternary ammonium compounds methscopolamine and glycopyrrolate.

As with all medications, anticholinergic medications have side effects. Consequences of excessive drying of the mucous membranes include overly dry mouth and dry or sore throat. Decreased perspiration due to drying of the skin can lead to temperature dysregulation. Eye effects include dilitation of the pupils with photophobia, loss of accommodation, blurred vision, and/or increased intraocular pressure, a particular concern for people with narrow-angle glaucoma. Systemic side effects include potential for increased heart rate, urinary retention, constipation, and gastrointestinal ileus. Dosing with these medications therefore requires judicious attention to achieve benefit and minimize risks and side effects.

A number of individual medications containing an oral anticholinergic agent have been marketed for treating the symptoms of allergic rhinitis. Examples of these are:

1. Hista-Vent® DA Exended Release Tablets, which contains: phenylephrine 20 mg; chlorpheniramine 8 mg; and methscopolamine nitrate 2.5 mg.
2. Atrohist® Plus, which contains: phenylepherine hydrochloride 25 mg, phenylepherine 50 mg, chlorpheniramine 8 mg, and hyoscyamine sulfate 0.19 mg; atropine sulfate 0.04 mg, and scopolamine hydrobromide 0.01 mg.

AlleRx® Dose Pack is a packaged rhinitis treatment regimen that contains a morning dosage that has 120 mg pseudoephedrine HCl and 2.5 mg of the non-sedating anticholinergic agent methscopolamine nitrate, and a nighttime dose containing the sedating antihistamine 8 mg chlorpheniramine maleate and 2.5 mg methscopolamine nitrate. It is licensed under U.S. Pat. No. 6,270,796 of Weinstein that teaches limitation of dosing of decongestant to the daytime hours to avoid excessive stimulation and nighttime insomnia. Notably, the AlleRx regimen utilizes anticholinergic agent both day and night and would result in the same anticholinergic dosing that would occur with a single dosage unit that was formulated with an anticholinergic agent.

In view of the noted side effects of anticholinergic agents, it would be preferable in some individuals to take advantage of the benefits of these drying agents without the requirement for persistent dosing around the clock. As noted, runny nose and/or constant clearing the throat may be considerably more intrusive during the daytime, social, or work hours for some individuals and control of these symptoms would be clearly more urgent than at night while sleeping.

It is a general pharmacotherapeutic principle to utilize medication as required to be effective and to avoid additional or unnecessary dosing to avoid side effects. The concept of dosing anticholinergic agents during the hours most needed, and not a times when it is less needed or not needed, is in accord with this concept. Limitation of dosing may be particularly helpful for individuals who are less tolerant of these agents, or of medication in general, yet are troubled with rhinorrhea or post nasal drip, or for individuals who are disposed to urinary/prostate or functional gastrointestinal disorders. In such individuals, dosing for the hours most needed and not at other times would be most suitable.

It is well known that individuals with rhinitis utilize rhinitis medications hundreds of millions of times a year. It is not uncommon for inappropriate choices to result in symptomatic worsening rather than improvement. There is a present need for preformulated regimens which advantageously use rhinitis medications in a manner to establish simplicity, reduce confusion, and increase convenience. While a number of rhinitis medications incorporate oral anticholinergic drying agents, no medication or medication regimen has been devised to instruct or otherwise alert a user to use anticholinergic agent during the waking hours and attenuate or not use such an agent during sleeping hours, such as to maximize therapeutic advantages and minimize side effects of such agents. Moreover, no such packaged regimen has been devised to make such treatments convenient and organized for a user.

SUMMARY OF THE INVENTION

It is therefore an object of the present invention to provide regimens for the treatment of rhinitis with rhinorrhea that utilize anticholinergic agent during the day, and attenuate or eliminate its dosing at night (the terms "day" and "night" are intended to be synonymous with times when awake, and asleep, such times varying in accordance with the schedule of the individual).

It is another object of the present invention to reduce confusion in the use of such regimens by incorporating them in a package with indicia to distinguish the day and night doses, and instructions for dosing.

The devising of such formulations and instructions requires pharmaceutical expertise and requires understanding of the actions, side effects, and pharmacokinetics of the formulated components, including components which effect the bioavailability of the active ingredients, as well as determination of the suitability of the components' use together. It is therefore another object of the present invention to provide a user with an expertly devised regimen.

It is a further object of the present invention to provide a method and device for organizing, storing, and coordinating regimens for the treatment of rhinitis with rhinorrhea that contain an anticholinergic agent for daytime dosing and attenuated or no dosing of such an agent at night for the purpose of convenience in using such regimens by providing such regimens in a prepackaged container which incorporates coordinating indicia and instructions.

It is still another object of the present invention to provide a user with an anticholinergic-containing rhinitis regimen that preferably contains a non-sedating or relatively non-sedating anticholinergic agent.

It is yet another object of the present invention to provide a user with anticholinergic-containing rhinitis regimens that preferably contains a non-sedating or relatively non-sedating anticholinergic agent and a non-sedating antihistamine (that has limited drying effect).

The present invention achieves these and other objectives by providing a treatment regimen for treating rhinitis with rhinorrhea, a pharmaceutical package for treating rhinitis with rhinorrhea, and a method of treating rhinitis with rhinorrhea. The treatment regimen includes a daytime dosage unit containing medication for treating rhinitis and an anticholinergic agent for treating rhinorrhea, and a nighttime dosage unit containing medication for treating rhinitis and an attenuated dosage of an anticholinergic agent for treating rhinorrhea or no anticholinergic agent. The pharmaceutical package includes a prefilled, unifying dispensing container containing at least two modules of different dosage units of medications for treating rhinitis with rhinorrhea where one dosage unit is for daytime dosing to maximize the therapeutic advantages of an anticholinergic agent and the other dosage unit is for nighttime dosing to minimize the side effects of the anticholinergic agent, indicia for distinguishing the daytime dosage unit and the nighttime dosage unit and signifying their use together, and coordinating instructions for their use. The container can have one of any number of forms, including, but not limited to, a box with the dosages in bottles, a blister package, or a box of individual blister packages.

Other objects of the present invention will become apparent in light of the following examples and the appended claims.

DETAILED DESCRIPTION OF THE PREFERRED EMBODIMENT

The following are representative regimens in accord with the present invention:

EXAMPLE 1

Daytime Dosage
120 mg pseudoephedrine HCl and 2.5 mg methscopolamine nitrate (12 hour dosage)
Nighttime Dosage
8 mg chlorpheniramine maleate
This regimen would have the anticholinergic agent methscopolamine in the daytime formulation, but not at night. Notably, chlorpheramine is a first-generation sedating antihistamine and, as noted, has anticholinergic drying properties itself. Dosing of such an agent is preferably avoided during the daytime unless sedation is desired at that time. Methscopolamine is considered a non-sedating agent, not crossing the blood-brain barrier easily. While a non-sedating agent is preferred, other agents having anticholinergic properties might likewise be incorporated.

EXAMPLE 2

Daytime Dosage
120 mg pseudoephedrine HCl and 2.5 mg methscopolamine nitrate (12 hour dosage)

Nighttime Dosage 180 mg fexofenadine (24 hour dosage)

This regimen would have the nonsedating anticholinergic agent methscopolamine in the daytime formulation and not at night. Fexofenadine utilized in this example is a second-generation non-sedating antihistamine and, as noted, does not have anticholinergic drying properties. Other non-sedating antihistamines might be similarly utilized. This regimen would be appropriate for an individual whose symptoms of rhinorrhea or post-nasal drip are bothersome during the day and relatively inconsequential at night allowing a reprieve from anticholinergic medication at night.

EXAMPLE 3

Daytime Dosage 120 mg pseudoephedrine HCl and 2.5 mg methscopolamine nitrate

Nighttime Dosage 180 mg fexofenadine and 1.25 mg methscopolamine

This regimen would have the nonsedating anticholinergic agent methscopolamine in the daytime formulation and an attenuated dosage of methscopolamine at night. This regimen would be appropriate for an individual whose symptoms of rhinorrhea or post-nasal drip are bothersome during the day and somewhat at night, necessitating a drying agent. It might also be useful for an individual who is symptomatic both day and night, but also experiences side effects of anticholinergic agents necessitating a lower dosage.

EXAMPLE 4

Daytime Dosage 120 mg pseudoephedrine HCl, 60 mg fexofenadine and 2.5 mg methscopolamine nitrate (12 hour dosage)

Nighttime Dosage 60 mg fexofenadine (12 hour dosage)

This regimen is similar to Example 2, however, the antihistamine fexofenadine is divided in the daytime and nighttime dosage.

EXAMPLE 5

Daytime Dosage 120 mg pseudoephedrine HCl and 2.5 mg methscopolamine nitrate (12 hour dosage)

Nighttime Dosage 60 mg pseudoephedrine HCl and 1.25 mg methscopolamine nitrate (12 hour dosage)

This regimen has no antihistamine and is intended for treatment of nasal congestion and rhinorrhea. It might be suitable for individuals with rhinorrhea due to viral respiratory tract infections ("colds") as the histamine mechanism is not a usual mechanism for cold symptoms. Notably, as decongestant can produce insomnia in some individuals, both decongestant pseudoephedrine and methscopolamine dosage are illustrated to be attenuated at night in this example.

The present invention is a treatment regimen, a pharmaceutical package containing a treatment regimen, and a method for treating rhinitis with rhinorrhea. The treatment regimen includes a daytime dosage unit containing medication for treating rhinitis and an anticholinergic agent for treating rhinorrhea to maximize the therapeutic advantages of the anticholinergic agent, and a nighttime dosage unit containing medication for treating rhinitis and an attenuated dosage of anticholinergic agent or no anticholinergic agent in order to minimize the side effects of the anticholinergic agent. The pharmaceutical package is a prefilled, unifying dispensing container containing at least two different dosage units of medications for treating rhinitis with rhinorrhea where one dosage unit is for daytime dosing and the other dosage unit is for nighttime dosing, indicia for distinguishing the daytime dosage unit and the nighttime dosage unit and signifying their use together, and instructions for coordinating the daytime dosage unit and the nighttime dosage unit as a treatment regimen for treating rhinitis with rhinorrhea. Such containers as boxes, packets or blister packs are well known in the art. The dosage units may be in the form of tablet, pill, capsule, caplet, powders, liquids, gels, some of which may require reconstituting, or any generally recognized oral form of medication.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A pharmaceutical package for treating rhinitis with rhinorrhea comprising:

a daytime oral dosage unit containing a non-sedating antihistamine for treating rhinitis and a non-sedating anticholinergic agent having limited capacity to cross blood-brain barrier for treating rhinorrhea;

a nighttime oral dosage unit containing a non-sedating antihistamine for treating rhinitis and a non-sedating anticholinergic agent that has limited capacity to cross blood-brain barrier and that is in a lower amount than the amount in the daytime dosage unit or no anticholinergic agent;

indicia to distinguish between the daytime dosage unit and the nighttime dosage unit;

instructions for coordinating the daytime dosage unit and the nighttime dosage unit as a treatment regimen for treating rhinitis with rhinorrhea; and a unifying container for housing the daytime dosage unit, the nighttime dosage unit, the indicia, and the instructions.

2. The pharmaceutical package of claim 1 wherein the medication for treating rhinitis includes a decongestant.

* * * * *